United States Patent [19]

Takacs et al.

[11] 4,308,399
[45] Dec. 29, 1981

[54] O-(3-AMINO-2-HYDROXY-PROPYL)-AMIDOXIME DERIVATIVES, PROCESS FOR THE PREPARATION THEREOF AND PHARMACEUTICAL COMPOSITIONS CONTAINING SAME

[75] Inventors: Kalman Takacs; Peter N. Literati; Ilona Kiss nee Ajzert; Antal Simay; Matyas Szentivanyi; Sandor Virag; Katalin Farago, all of Budapest, Hungary

[73] Assignee: Chinoin Gyogyszer es Vegyeszeti Termekek Gyara Rt., Budapest, Hungary

[21] Appl. No.: 54,791

[22] Filed: Jul. 5, 1979

Related U.S. Application Data

[62] Division of Ser. No. 892,148, Aug. 30, 1977, Pat. No. 4,187,220.

[51] Int. Cl.³ .................. C07D 295/14; C07D 401/12; C07D 403/12; C07D 401/13
[52] U.S. Cl. .............................. 564/257; 260/326.52; 260/348.44; 260/239 B; 544/124; 544/128; 544/140; 544/162; 546/23; 546/145; 546/176; 546/193; 546/194; 546/211; 548/215; 424/327; 424/258; 424/263; 424/264; 424/273 P; 564/229; 564/256
[58] Field of Search ................. 260/566 AE; 564/256, 564/257, 229

[56] References Cited
U.S. PATENT DOCUMENTS 3,751,312 8/1973 Wright et al. ............... 260/566 AE
4,038,317 7/1977 Wermuth et al. ........... 260/566 AE Primary Examiner—Donald G. Daus
Assistant Examiner—James H. Turnipseed
Attorney, Agent, or Firm—Karl F. Ross

[57] ABSTRACT

A compound effective in the treatment of diabetic angiopathy, i.e. a selective β-receptor blocker has the formula

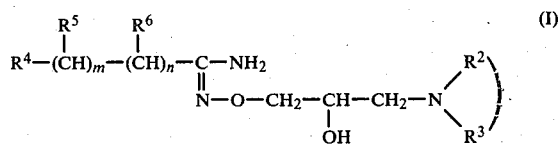

wherein:

$R^2$ is a hydrogen or alkyl having one to five carbon atoms, $R^3$ is alkyl having one to five carbon atoms, cycloalkyl or phenyl optionally substituted with hydroxyl or phenyl, or $R^2$ and $R^3$ together form a five- to eight-membered ring optionally containing also other heteroatoms and/or fused with another ring, preferably phenyl, naphthyl, quinolyl, isoquinolyl, pyridyl, pyrazolyl, $R^5$ is hydrogen or alkyl having one to four carbon atoms, cycloalkyl or phenyl optionally substituted with halogen, alkoxy having one to four carbon atoms or alkyl having one to four carbons, $R^6$ is hydrogen, alkyl having one to four carbon atoms or phenyl, m=0, 1 or 2, and n=0, 1 or 2.

10 Claims, No Drawings

O-(3-AMINO-2-HYDROXY-PROPYL)-AMIDOXIME DERIVATIVES, PROCESS FOR THE PREPARATION THEREOF AND PHARMACEUTICAL COMPOSITIONS CONTAINING SAME

This application is a division of application Ser. No. 892,148 filed Aug. 30, 1977 and issued Feb. 5, 1980 as U.S. Pat. No. 4,187,220.

The present invention relates to new amidoxime derivatives and pharmaceutically acceptable salts thereof. In a further aspect this invention relates to pharmaceutical compositions comprising one or more of the above compounds of the invention, and to methods of treating diabetic angiopathy and in some instances hypertension in mammals. Some of the compounds of the invention show also co-blocking activity.

Diabetes mellitus is one of the most common metabolic diseases, and its main symptom is the disorganization of the carbohydrate metabolism balance in the organism. This symptom is, however, often accompanied by pathological vascular disorders, for instance extremital vascular stenoses, pathological changes in the vessels of the eye ground etc. At the present time there are numerous compounds known in the art including insulin for decreasing of hyperglycaemia but in the treatment of diabetic angiopathy, which is a concomitant disease, the results are only moderate when using the known, commercially available pharmaceutical preparations. The reason for this is that as a consequence of diabetes mellitus the adrenergic receptor sites of the vessels undergo essential changes, and therefore the adrenergic reactions induced by the pharmaceutical preparations in a diabetic are different from those in a non-diabetic organism [Nature New Biology, 243, No. 130, 276 (1973); Szemészet, 111, 23 (1974); Endocrinology, 93, 752 (1973)]. Upon quantitative increase of metabolism the $\alpha$-adrenergic receptor sites of the vessels are transformed into $\beta$-receptors. The receptor-transformation is due to a modulator compound [Amer. J. Physiol., 218, 869 (1970)]. When this compound is added to an $\alpha$-receptor the $\alpha$-antagonists are no longer effective since the receptor has been transformed into $\beta$-receptor. The original $\alpha$-sensitivity can be restored by adding also a $\beta$-blocker.

In cases where a qualitative change appeared in the metabolism it has been found that the $\alpha$-antagonists (e.g. noradrenaline) preserve their activity but their effect can be inhibited by $\beta$-blockers. This is the first functional change appearing in a diabetic organism and can be detected even about 24 hours after the administration of alloxan (hexahydrotetraketo-pyrimidine). The source of the changes characteristic of diabetes is an imperfect $\alpha$-$\beta$ receptor transformation caused by the formation of an irregular modulator.

We have now discovered that certain amidoxime derivatives and pharmaceutically acceptable salts thereof show no effect or a slight effect on the adrenergic reactions of the healthy vessels while having a strong influence on the adrenergic receptors which are subject to pathological change due to the diabetes mellitus.

In summary the compounds of this invention can be represented by the formula I

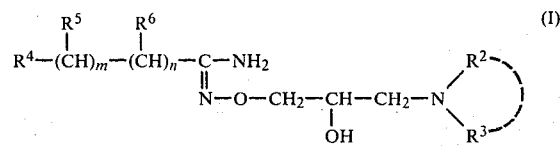

wherein
$R^2$ is hydrogen or alkyl having one to five carbon atoms;
$R^3$ is alkyl having one to five carbon atoms, cycloalkyl or phenyl which can be substituted with hydroxyl or phenyl; or
$R^2$ and $R^3$ together can form a five- to eight-membered ring which also can contain other heteroatoms and/or fused with another ring;
$R^4$ is cycloalkyl, aromatic or heteroaromatic group, which can be substituted with one or more halogens, alkoxy or alkyl and/or fused with another ring such as phenyl, naphthyl, quinolyl, isoquinolyl, pyridyl, or pyrazolyl;
$R^5$ is hydrogen or alkyl having one to four carbon atoms, cycloalkyl or phenyl which can be substituted with halogen, alkoxy having one to four carbon atoms or alkyl having one to four carbon atoms;
$m = 0$, 1 or 2;
$n = 0$, 1 or 2; and
$R^6$ is hydrogen, alkyl having one to four carbon atoms or phenyl.

A preferred feature of the invention includes compounds as defined above wherein $R^2$ and $R^3$ form together with the nitrogen atom to which they are attached a piperidino group, $R^4$ is a phenyl or pyridyl substituted with 1 or 2 alkoxy groups having 1 to 4 carbon atoms and $R^5$, $R^6$, m and n have the same meanings as indicated above.

Also encompassed within the invention are pharmaceutically acceptable salts of the above compounds.

The compounds of the invention have a selective $\beta$-blocking activity, and therefore find application in the treatment of diabetic angiopathy. Some of the compounds within the scope of the invention are also useful hypotensive agents and/or possess an $\alpha$-blocking activity.

Typical illustrations of the compounds of the formula I, and salts thereof, are found below by reference to Examples 1 to 33. The preferred —NR$^2$R$^3$ group is the piperidino group, and the preferred $R^4$ substituents are phenyl or pyridyl substituted with an alkoxy. The particularly preferred compounds of the formula I are: O-(3-piperidino-2-hydroxy-1-propyl)-3,4-dimethoxyphenyl-acetamidoxime dihydrochloride; and O-(3-piperidino-2-hydroxy-1-propyl)-nicotinamidoxime dihydrochloride.

The compounds of the formula I and the pharmaceutically acceptable salts thereof can be prepared by reacting (a) amidoximes of the formula II

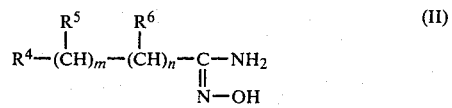

wherein $R^4$, $R^5$, $R^6$, n and m are as defined above, with amines of the formula IIIA or IIIB

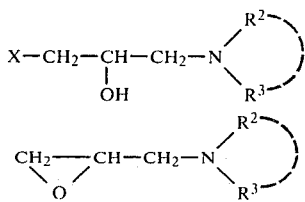

wherein $R^2$ and $R^3$ are as defined above, and X is halogen,
in the presence of a base; or
(b) amidoximes of the formula II, wherein $R^4$, $R^5$, $R^6$, m and n are as defined above, with epichlorohydrine, and reacting the amidoximes of the formula V

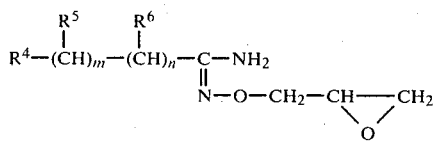

initially obtained, after or without separation, with amines of formula IV

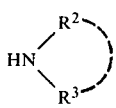

wherein $R^2$ and $R^3$ are as defined above; or
(c) the alkali metal salts of the amidoximes of the formula II,
wherein $R^4$, $R^5$, $R^6$, n and m are as defined above, with 2-phenyl-3-substituted-5-chloromethyl-oxazolidines of the formula VI

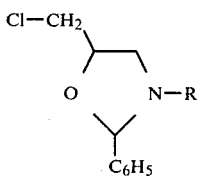

wherein R has the same meaning as given for $R^2$ and $R^3$ except hydrogen,
and hydrolyzing the compounds of the formula VII

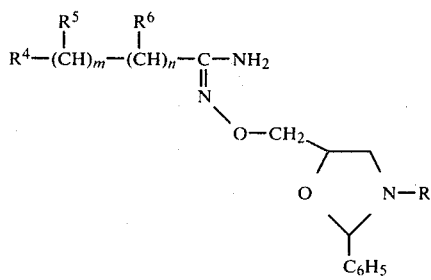

without isolation; said steps (a), (b) or (c) being optionally followed by transforming the compounds of the formula I initially obtained into the pharmaceutically acceptable salts thereof with suitable organic or inorganic acids and/or liberating the free bases from the salts initially obtained.

The compounds of the formula III can be prepared by reacting epichlorohydrin with amines in a manner known per se.

Procedure (a) can be effected by conducting the reaction in an aqueous medium; in an organic solvent containing water (e.g. in aqueous solution of alcohol); or inorganic solvents, preferably at about from 0° to 140° C.

One can also proceed reacting the amidoximes of the formula II with alkali alcoholates in a dry medium, and adding the alcoholic solution of the amines of the formula III to the solution containing the amidoxime salts formed, dropwise. The reaction is preferably carried out in the range from about 0° to 100° C., under stirring.

According to a further alternative the salts of the amidoximes of the formula II are prepared with alkali hydroxides, preferably sodium or potassium hydroxide, in a non-water-miscible organic solvent, e.g. benzene, toluene, xylene. The salt formation is effected at the boiling temperature of the solvent, the water deliberated is removed from the system by aseotropic distillation, the solution of the amines of the formula III is subsequently added and the reaction mixture is boiled for a further definite period.

According to a further embodiment of the process (a) the reaction is performed in an aqueous medium, by adding the alkaline aqueous solution or suspension of the amidoximes to the compounds of the formula III, under stirring. The reaction is preferably conducted in the range of about from 0° to 60° C., and the amidoxime is preferably dissolved or suspended in a 5 to 20% aqueous sodium hydroxide solution. The reaction can be accomplished also in an organic solvent-water mixture, for example by adding the alkaline aqueous solution or suspension of the amidoxime to the alcoholic or dioxane solution of a compound of the formula III, dropwise. The reaction can be carried out also in a reverse order, when to the alkaline aqueous solution or suspension of the amidoxime the other compound is added.

According to the process (b) of the invention amidoximes of the formula II are reacted with epichlorohydrin in the presence of a base. If desired, the epoxide compound formed during the reaction can be separated. However, it is more favorable to effect the reaction in one synthesis step, without recovering the intermediate. The reaction is carried out in an aqueous or organic medium; in an organic solvent containing water; or in the co-existence of two solvent phases, at a temperature of about from −10° to about +100° C.

According to an embodiment of this process the reaction is performed in an alkaline aqueous medium, by adding to the alkaline aqueous solution or suspension of the amidoximes 1 to 4 moles of epichlorohydrin. The addition of the epichlorohydrin is carried out at −10° to +60° C., under stirring, in one or more portions, or by dropwise addition. The order of the addition can be reversed so that either the alkaline aqueous solution or suspension of the amidoxime is added to the epichlorohydrin, or the amidoxime is added to the alkaline aqueous solution or suspension of the epichlorohydrin. The intermediate of the formula V can be removed by extracting with a non-water-miscible solvent. It is, however, more favorable to react the intermediates of the formula V with the corresponding amines without previous separation.

If the oxime starting substance is slightly soluble in the alkaline aqueous solution, the reaction can also be effected in an organic solvent containing water, e.g. in aqueous alcohols or aqueous dioxane. If desired, the reaction can be conducted also in the co-existence of two solvent phases or in the presence of an emulsifying agent, by dissolving the epichlorohydrin in a non-water-miscible organic solvent, for example in benzene or ether, adding the solution obtained to the alkaline aqueous solution or suspension of the amidoxime. The order of the addition of the reactants can be reversed also in this case.

The process (b) of the invention can be effected also in dry solvents, preferably in dry alcohols. In this case an alkali metal salt of the amidoxime is prepared, preferably by dissolving the amidoxime in the alcohol solution of an alkali alcoholate. After the addition of the epichlorohydrin the reaction mixture is allowed to stand at 0° to 20° C. for one to five days, whereupon the suitable amine is added and the reaction is conducted at room temperature or under heating the reaction mixture. As dry solvents aside from alcohols also other organic solvents, for example, acetone, dimethyl sulfoxide, dimethyl formamide or mixtures thereof can be employed.

When carrying out process (c) as alkali metal salts of the amidoximes of the formula II preferably sodium salts are used, and the reaction is preferably accomplished in alkanols. The hydrolysis of the intermediates of the formula VII is preferably carried out with acids. The compounds of the VI can be prepared by applying the procedure described in the DT OS-2 018 263.

The products of the formula I can be separated and purified according to conventional procedures, such as for example by crystallization or extraction when an aqueous medium is used. If an organic solvent is employed, the product is crystallized or the solvent is evaporated and the product is subsequently washed with water and dried. The products can be also recovered in the form of the salts thereof, or salts can be formed from the bases separated by treating with one or two equivalents of a mineral acid or organic acid, preferably with pharmaceutically acceptable, non-toxic acids. Also the free bases can be liberated from the salts obtained.

The compounds of the formula I have been evaluated as general $\beta$-blockers by assay using trachea-ring preparations [J. Pharmacol. Exp. Therap., 90, 104 (1974)] and papillary muscles of cats.

The assays of selective $\beta$-blocking activity on rat aorta-spiral preparations were carried out in the following way:

The thorax of the animal was opened and the thoracic aorta taken out and cut spirally. The motions of the straightened spiral were recorded with an isotonic recorder on two sooted cylinders. On the first cylinder the reactions of the control and on the second one the reactions of the rat-aorta treated with Streptosoticine [2-(3-nitroso-3-methyl-ureido)-2-desoxi-D-glucose] were recorded. The reaction was positive when the dose-effect curve of the noradrenaline was not influenced by the tested compound on the control preparation, while on the diabetic aorta the effect was inhibited. The compounds of the present invention generally showed a selective activity, which meant a strong $\beta$-blocking effect on diabetic aortas and no or slight effect on normal tests. Some of the tested compounds showed $\alpha$-blocking activity on normal aortas.

Testing the product of the Example 2 [O-(3-piperidino-2-hydroxy-1-propyl)-3,4-dimethoxyphenyl-acetamidoxime dihydrochloride] gave the following results:

The $pD_2$-values (negative logarithm of the dose corresponding to half of the maximum effectivity) were evaluated. The average of five subsequent tests calculated from the difference of the $pD_2$-values on diabetic aorta-spiral was $\bar{x}=1.31$. The corresponding value on normal spiral was $\bar{x}=0.52$. On guinea pig trachea 10 $\gamma$ of the tested substance decreased the effect of 0.01 $\gamma$/ml. isoprenaline [D,L-1-(3,4-dihydroxyphenyl)-2-isopropylamino-ethanol] to half of its original level. On a rat uterus pretreated with Streptosotocine the tested compound had no effect when employed in a concentration of 100 $\gamma$/ml. In a concentration of 50 $\gamma$/ml. the tested compound set in motion the uterus preparat of the untreated rat, which was stopped by noradrenaline. This effect is identical with the effect of 0.5 $\mu$g/ml inderal [1-isopropylamino-3-(1-naphthyloxy)-propane-2-ol]. On isolated strips of rat gastric fundus treated with Streptosotocine the tested compound showed no effect in a concentration of 10 $\gamma$/ml., contrary to 0.01 $\gamma$/ml. of isoprenaline, where a relaxation of 25 mm. was observed. On isolated strips of rat gastric fundus which was not pretreated even 100 $\gamma$/ml. concentration of the test compound had no effect on the dose-effect curve of the isoprenaline, which means that it showed a strong $\beta$-blocking effect on diabetic samples and a slight effect on normal tests.

The hypoxia survival time was extended with one order of magnitude by the test compound.

The isoprenaline induced tachycardia was also slightly influenced by the tested compound. 5 minutes after the administration of a 10 mg./kg. i.v. dose the heart frequency increased by 10%, and 5 minutes after the adiminstration of a 100 mg./kg. i.v. dose it decreased by 3%.

The tests carried out on the product of the Example 5 [O-(3-piperidino-2-hydroxy-1-propyl)-nicotamidoxime dihydrochloride] gave the following results:

The mean-value calculated from the differences of the $pD_2$-values on diabetic aorta-spiral was $\bar{x}=1.25$. The corresponding value in the control test was $\bar{x}=0.57$. The test compound used in a concentration of 50 $\gamma$/ml. decreased the effect of 0.001 $\gamma$/ml. isoprenaline from 16 mm. to 5 mm. When employed in a concentration of 100 $\gamma$/ml., it entirely compensated the effect of 0.001 $\gamma$/ml. isoprenaline, and decreased the effect of 0.01 $\gamma$/ml. isoprenaline from 28 mm. to 19 mm.

Tests were carried out to determine whether the noradrenaline induced contractions on the aorta-spiral preparations of diabetic animals treated with Streptosotocine and untreated, respectively could be compensated with inderal. For control those animals were chosen in which no receptor transformation took place. In case of the animals treated with Streptosotocine the mean difference between the $pD_2$-values (before and after the administration of inderal) of the dose-effect curves of the noradrenaline were as follows: $x=1.0335$; $Sx=0.0829$; $t=3.5885$; $p<0.01$; $n=8$. On non-diabetic preparations the inderal had no effect on the noradrenaline induced contractions.

Tests were carried out to evaluate if a compound could be found among the compounds structurally close to the $\beta$-blockers which has an effect on the aorta-spiral of a diabetic animal similar to that of the inderal without exerting any substantial influence on the normal $\beta$-reactions. In other words a compound having a specific effect on the modified β-effect appearing in diabetic vessels was searched for. In the following test the compounds of the invention tested are as follows:

NP-18: O-(3-piperidino-2-hydroxy-1-propyl)-3,4-dimethoxy-phenyl-acetamidoxime dihydrochloride NP-51: O-(3-piperidino-2-hydroxy-1-propyl)-nicotamidoxime dihydrochloride.

On the aorta-spiral of animals treated with Streptosotocine the difference between the $pD_2$-values before and after administering a 1 μg./ml. dose of "NP-18" was: $\bar{x}=0.6422$; $S\bar{x}=0.129$; $t=4.9783$; $p<0.01$; $n=6$.

We found that if the initial receptor transformations are inhibited by adding compounds "NP-18" or "NP-51", the final histological changes do not occur. About 60% of the rats belonging to the CFY strain used during the tests were in a latent diabetic state which was detected in sugar-loading tests. On one part of these animals (weight=4 to 500 g.) diabetic macro- and microangiopathy was detected. In the animals which were treated with the compounds "NP-18" or "NP-51" at weight of 200 g. microangiopathy did not develop till they reached the weight of 500 g. and the degree of the macroangiopathy was also considerably smaller.

It was also found that although "NP-18" and "NP-51" inhibited the effect of isoprenaline on guinea pig trachea, they exerted an effect smaller by 4 orders of magnitude than inderal. These compounds did not show any significant effect on the blood pressure, heart frequency, minute volume and dp./dt. value of anesthetized cats. They did not influence the effect of isoprenaline in respect of the above parameters and caused bradycardia and dp./dt. decrease only in a dose of 100 μg./kg. The effect was similar to that of a 0.5 μg./kg. inderal dose.

The difference between the β-blocking activity of the new compounds of the general formula I and the inderale on cat papillary muscle was also four orders of magnitude. They exerted an influence in guinea pig ileum on the effect of barium chloride and acetylcoline only in a dose of 50 to 100 μg./ml. Neither the compound "NP-18" nor the compound "NP-51" had any influence on the hanging of mice on a rotating rod.

$LD_{50}$ NP-18: 165 mg./kg. i.v. mouse. NP-51: 123 mg./kg. i.v. mouse.

The compounds of the formula I and their pharmaceutically acceptable salts find their application in therapy in form of pharmaceutical preparations in which the active ingredient is accompanied by the conventional pharmaceutical carriers. The preparations can be in tablet, dragee, injection or capsule form.

Further details of the invention are to be found in the following non-limiting Examples:

EXAMPLE 1

2.3 g. of sodium are dissolved in 200 ml. of abs. ethanol and 13.6 g. of benzamidoxime are added. The solution of 3-piperidino-2-hydroxy-1-chloro-propane in 50 ml. of abs. ethanol—prepared from 9.3 g. of epichlorohydrine and 8.5 g. of piperidine in a manner known per se—is then added dropwise at the boiling temperature of the mixture. The reaction mixture is refluxed for eight hours, filtered, and the solvent is evaporated in vacuo. To the residue 100 ml. of 5% sodium hydroxide solution are added, and the oily product is extracted with benzene. Upon evaporating the benzene extract 9.2 g. of O-(3-piperidino-2-hydroxy-1-propyl)-benzamidoxime are obtained, melting at 97° C. (from diisopropyl ether). Molecular weight: 277.35.

Elemental analysis: Calculated: C=64.95%; H=8.36%; N=15.15%; Found: C=64.69%; H=8.46%; N=14.87%.

The dihydrochloride salt of the product is precipitated from isopropanol solution by introducing hydrochloric acid gas or adding the alcohol solution of hydrochloric acid. Melting point: 212° to 214° C. (isopropanol). Molecular weight: 350.29.

Elemental analysis for $C_{15}H_{25}N_3O_2Cl_2$: Calculated: $Cl^-=20.24\%$; Found: $Cl^-=19.90\%$.

$LD_{50}=70.5$ mg./kg. i.v. on mice.

The nicotinic acid salt of the product obtained is prepared in abs. ethanol solution by adding benzine, when the salt crystallizes. Melting point: 112° C. (from methyl ethyl ketone). Molecular weight: 400.46.

Elemental anaylsis for $C_{21}H_{28}N_4O_4$: Calculated: C=62.98%; H=7.05%; N=14.00%; Found: C=62.84%; H=7.11%; N=13.76%.

The dihydrochloride salt showed a slight α-blocking activity on normal objects and a strong β-blocking activity on diabetic tests which were carried out as described in the introductory part of the specification.

$LD_{50}=70.5$ mg./kg. i.v. on mice.

EXAMPLE 2

Following the procedure described in Example 1 but starting from 3,4-dimethoxy-phenyl-acetamidoxime and 3-piperidino-2-hydroxy-1-chloro-propane, O-(3-piperidino-2-hydroxy-1-propyl)-3,4-dimethoxyphenyl-acetamidoxime dihydrochloride is prepared. Melting point: 202° to 203° C. (from abs. ethanol). Molar weight: 424.38.

Elementary analysis for $C_{18}H_{31}N_3O_4Cl_2$: Calculated: C=50.94%; H=7.36%; N=9.90%; Cl=16.71%; Found: C=50,80%; H=7.57%; N=9.84%; Cl=16.42%.

$LD_{50}=165$ mg./kg. i.v. (on mice).

On trachea-spiral and papillary muscle a slight β-blocking activity can be observed. The effect on papillary muscle at a temperature of 100 μg./ml. is identical with the effect caused by 0.05 μg./ml. of inderal. On the gastric fundus in a concentration of 100 μg./ml. the compound does not have any influence on the activity of isoprenaline. At the aorta spiral of a diabetic animal, however, an inhibition of one order of magnitude was observed.

EXAMPLE 3

Following the procedure described in Example 1 but starting from 3,4-dimethoxyphenyl-acetamidoxime and 3-(1,2,3,4-tetrahydro-2-isoquinolyl)-2-hydroxyl-1-chloropropane O-/3-(1,2,3,4-tetrahydro-2-isoquinolyl)-2-hydroxy-1-propyl/-3,4-dimethoxyphenyl-acetamidoxime dihydrochloride is prepared. Melting point: 189° C. (from isopropanol). Molecular weight: 472.40.

Elemental analysis for $C_{22}H_{31}N_3O_4Cl_2$: Calculated: C=55.93%; H=6.61%; N=8.89%; Cl=15.01%; Found: C=55.89%; H=6.82%; N=8.64%; Cl=14.75%.

EXAMPLE 4

Following the procedure described in Example 1 but starting from 3,3-diphenyl-propionamidoxime and 3-piperidino-2-hydroxy-1-chloro-propane O-(3-piperidino-2-hydroxy-1-propyl)-3,3-diphenyl-propionamidoxime dihydrochloride is obtained. Melting point: 228° to 230° C. (from isopropanol).

Elementary analysis for $C_{23}H_{33}N_3O_2Cl_2$: Calculated: C=60.79%; H=7.32%; N=9.25%; Cl=15.60%; Found: C=60.45%; H=7.25%; N=8.94%; Cl=15.79%;

EXAMPLE 5

Following the procedure described in Example 1 but starting from nicotinamidoxime and 3-piperidino-2-hydroxy-1-chloro-propane O-(3-piperidino-2-hydroxy-1-propyl)-nicotinamidoxime dihydrochloride is prepared. Melting point: 204° C. (from abs. ethanol). Molecular weight: 351.27.

Elemental analysis for $C_{14}H_{24}N_4O_2Cl_2$: Calculated: C=47.87%; H=6.89%; N=5.95%; Cl=20.19%; Found: C=47.59%; H=7.00%; N=15.64%; Cl=19.89%.

$LD_{50}$=123 mg./kg. i.v. (on mice). The product of this Example showed a slight β-blocking activity on normal test.

The nicotinic acid salt of the product is precipitated from ethyl acetate. Melting point: 111° C. (from ethyl acetate). Molecular weight: 401.46.

Elemental analysis for $C_{20}H_{27}N_5O_4$: Calculated: C=59.83%; H=6.77%; N=17.44%; Found: C=59.80%; H=6.92%; N=17.23%:

$LD_{50}$=250 mg./kg. i.v. (on mice). The product shows a strong β-blocking activity on a diabetic aorta spiral.

EXAMPLE 6

To 17.8 g. of 3-piperidino-2-hydroxy-1-chloropropane the solution of 10.45 g. of 3,4-dimethoxyphenyl-acetamidoxime in 40 ml. of 10% sodium hydroxide—prepared with heating—is added, at room temperature, under stirring, dropwise in half an hour. The reaction mixture is stirred at room temperature for eight hours and allowed to stand overnight. The oily product obtained is extracted with benzene, the extract is dried over sodium sulfate and the solvent is evaporated. From the ethyl acetate solution of the remaining 10.5 g. of O-(3-piperidino-2-hydroxy-1-propyl)-3,4-dimethoxyphenyl-acetamidoxime dihydrochloride crystallizes upon introducing hydrochloric acid gas. The product is identical with the product of Example 2. Melting point: 201° to 203° C.

EXAMPLE 7

To the benzene solution of 8.8 g. of 3-piperidino-2-hydroxy-1-chloro-propane the solution of 5.2 g. of 3,4-dimethoxyphenyl-acetamidoxime in 40 ml. of 10% sodium hydroxide solution—prepared under heating—is added at room temperature, under stirring, dropwise, in half an hour. The reaction mixture is stirred at room temperature for further eight hours and allowed to stand overnight. The benzene phase is separated and the aqueous phase extracted with benzene. The benzene solution is dried over sodium sulfate and the solvent is evaporated. From the residue using the method set forth in Example 6 for preparation of the hydrochloric acid salt, O-(3-piperidino-2-hydroxy-1-propyl)-3,4-dimethoxyphenyl-acetamidoxime dihydrochloride salt is obtained. The compound is identical with the product of Example 2.

EXAMPLE 8

To 8.8 g. of 3-piperidino-2-hydroxy-1-chloro-propane the solution of 5.2 g. of 3,4-dimethoxyphenyl-acetamidoxime in 40 ml. of 10% sodium hydroxide solution and 40 ml. methanol is added under stirring, dropwise for half an hour, the mixture is stirred at room temperature for subsequent eight hours and allowed to stand overnight. After evaporating the methanol the extraction with benzene and the salt forming reaction is carried out as described in Example 7. O-(3-piperidino-2-hydroxyl-1-propyl)-3,4-dimethoxyphenyl-acetamidoxime dihydrochloride is obtained which is identical with the product of Example 2.

EXAMPLE 9

To 2.72 g. of benzamidoxime 40 ml. of benzene and 0.8 g. of powdered sodium hydroxide are added. The reaction mixture is boiled for one hour under water separator and 4.5 g. of 3-piperidino-2-hydroxy-1-chloro-propane in 10 ml. of benzene are added to the boiling mixture dropwise. After boiling for 12 hours the solvent is evaporated and 20 ml. of 10% sodium hydroxide solution are added to the residue. The oily substance obtained is extracted with benzene and the benzene solution is evaporated. 3.6 g. of O-(3-piperidino-2-hydroxy-1-propyl)-benzamidoxime are obtained. The compound is identical with the product of Example 1.

EXAMPLE 10

To a sodium ethylate solution prepared from 2.3 g. of sodium and 200 ml. of abs. ethanol 15.5 g. of 4-chloro-benzamidoxime are added and subsequently 9.3 g. of epichlorohydrine are added dropwise at 0° to +10° C. The reaction mixture is stirred at 0° to +10° C. for eight hours and allowed to stand overnight at this temperature. The sodium chloride precipitated is filtered off, to the filtrate 8.6 g. of piperidine are added under stirring dropwise and the mixture is stirred for subsequent eight hours at room temperature. The reaction mixture is heated to boiling point and the solvent is evaporated in vacuo. 50 ml. of 5% sodium hydroxide solution is added to the residue and the oily substance is extracted with benzene. The benzene solution is dried over sodium sulfate, evaporated and the residue dissolved in alcohol. Upon introducing hydrochloric acid gas or adding hydrochloric acid in alcohol 11.0 g. of O-(3-piperidino-2-hydroxy-1-propyl)-4-chloro-benzamidoxime dihydrochloride are obtained. Melting point: 215° to 217° C. (from abs. ethanol). Molecular weight: 384.73.

Elemental analysis for $C_{15}H_{24}N_3O_2Cl_3$: Calculated: C=46.83%; H=6.29%; N=10.92%; Found: C=46.57%; H=6.41%; N=10.58%.

The product shows a slight β-blocking activity on normal test and a strong β-blocking activity on diabetic test.

EXAMPLE 11

Following the procedure described in Example 10 but starting from phenylacetamidoxime using diethyl amine as amine component O-(3-diethylamino-2-hydroxy-1-propyl)-phenylacetamidoxime dihydrochloride is prepared. Melting point: 156° to 158° C. (from isopropanol). Molecular weight: 352.30.

Elemental analysis for $C_{15}H_{27}N_3O_2Cl_2$: Calculated: C=51.14%; H=7.73%; N=11.93%; Cl=20.12%; Found: C=50.89%; H=7.65%; N=11.83%; Cl=20.10%.

EXAMPLE 12

Following the procedure described in Example 10 but starting from phenylacetamidoxime and using piperidine as amine component O-(3-piperidino-2-hydroxy-1-propyl)-phenylacetamidoxime dihydrochloride is obtained. Melting point: 198° to 200° C. (from abs. ethanol). Molecular weight: 364.31.

Elemental analysis for $C_{16}H_{27}N_3O_2Cl_2$: Calculated: C=52.75%; H=7.47%; N=11.54%; Cl=19.47%; Found: C=52.40%; H=7.51%; N=11.20%; Cl=19.85%.

EXAMPLE 13

Following the procedure described in Example 10 but starting from 4-chlorophenyl-acetamidoxime and using morpholine as amine component O-(3-morpholino-2-hydroxy-1-propyl)-4-chlorophenyl-acetamidoxime dihydrochloride is obtained. Melting point: 175° to 178° C. (from abs. ethanol). Molecular weight: 400.73.

Elemental analysis for $C_{15}H_{24}N_3O_3Cl_3$: Calculated: C=44.96%; H=6.04%; N=10.48%; Cl=26.54%; Found: C=45.20%; H=6.10%; N=10.52%; Cl=26.50%.

EXAMPLE 14

Following the procedure described in Example 10 but starting from 3,3-diphenyl-propionamidoxime and using isopropylamine as amine component O-(3-isopropylamino-2-hydroxy-1-propyl)-3,3-diphenyl-propionamidoxime dihydrochloride is prepared. Melting point: 179° C. (from acetone/water mixture). Molecular weight: 428.39.

Elemental analysis for $C_{21}H_{31}N_3O_2Cl_2$: Calculated: C=58.87%; H=7.29%; N=9.81%; Cl=16.55%; Found: C=58.58%; H=7.39%; N=9.53%; Cl=16.70%.

$LD_{50}=16.25$ mg./kg. i.v. (on mice). The compound possesses a strong β-blocking effect on diabetic aorta spiral.

EXAMPLE 15

Following the procedure described in Example 10 but starting from 3,3-diphenyl-propionamidoxime and using diethylamine as amine component O-(3-diethylamino-2-hydroxy-1-propyl)-3,3-diphenyl-propionaminoxime dihydrochloride is prepared. Melting point: 225° C. (from isopropanol). Molecular weight: 442.42.

elemental analysis for $C_{22}H_{33}N_3O_2Cl_2$: Calculated: C=59.72%; H=7.52%;, Cl=16.03%; Found: C=59.68%; H=7.55%; Cl=16.07%.

EXAMPLE 16

Following the procedure described in Example 10 but starting from 3,3-diphenyl-propionamidoxime and using 2-methylamine-ethanol as amine component O-[3-N-methyl-N-(2-hydroxy-ethyl)-amino-2-hydroxy-1-propyl]-3,3-diphenyl-propionamide dihydrochloride is prepared. Melting point: 175° C. (from isopropanol). Molecular weight: 444.39.

Elemental analysis for $C_{21}H_{31}N_3O_3Cl_2$: Calculated: C=56.78% ; H=7.03%; N=9.45%; Cl=15.95%; Found: C=56.40%; H=7.09%; N=9.14%; Cl=15.92%.

$LD_{50}=37$mg./kg. i.v. (on mice). The compound shows a strong β-blocking activity on diabetic aorta spiral.

EXAMPLE 17

Following the procedure described in Example 10 but starting from 3,3-diphenyl-propionamidoxime and using pyrrolidine as amine component O-(3-pyrrolidino-2-hydroxy-1-propyl)-3,3-diphenyl-propionamidoxime dihydrochloride is obtained. Melting point: 218° C. (from isopropanol). Molecular weight: 440.40.

Elemental analysis for $C_{22}H_{31}N_3O_2Cl_2$: Calculated: C=59.99%; H=7.10%; Cl=16.10%; Found: C=59.63%; H=7.32%; Cl=16.44%.

EXAMPLE 18

Following the procedure described in Example 10 but starting from 3,3-diphenyl-propionamidoxime and using piperidine as amine component O-(3-piperidino-2-hydroxy-1-propyl)-3,3-diphenyl-propionamidoxime dihydrochloride is prepared. The compound is identical with the product of Example 4. Melting point: 228° to 230° C. (from isopropanol).

EXAMPLE 19

Following the procedure described in Example 10 but starting from 3,3-diphenyl-propionamidoxime and using heptamethylene imine as amine component O-(3-heptamethyleneamino-2-hydroxy-1-propyl)-3,3-diphenyl-propionamidoxime dihydrochloride is prepared. Melting point: 233° C. (from isopropanol). Molecular weight: 482.48.

Elemental analysis: Calculated: C=62.24%; H=7.73%; Cl=14.70%; Found: C=61.97%; H=7.70%; Cl=14.74%.

EXAMPLE 20

Following the procedure described in Example 10 but starting from 3,3-diphenyl-propionamidoxime and using morpholine as amine component O-(3-morpholino-2-hydroxy-1-propyl)-3,3-diphenyl-propionamidoxime dihydrochloride is prepared. Melting point: 225° C. (from isopropanol). Molecular weight: 456.40.

Elemental analysis for $C_{22}H_{31}N_3O_3Cl_2$: Calculated: C=57.89%; H=6.85%; N=9.20%; Cl=15.53%; Found: C=57.66%; H=7.13%; N=8.95%; Cl=15.15%.

EXAMPLE 21

Following the procedure described in Example 10 but starting from 1-naphthyl-acetamidoxime and using diethyl amine as amine component O-(3-diethylamino-2-hydroxy-1-propyl)-1-naphthyl-acetamidoxime hydrochloride is prepared. Melting point: 150° to 152° C. (from abs. ethanol). Molecular weight: 365.89.

Elemental analysis for $C_{19}H_{28}N_3O_2Cl$: Calculated: C=62.36%; H=7.71%; N=11.49%; Cl=9.69%; Found: C=62.07%; H=8.00%; N=11.29%; Cl=9.63% .

EXAMPLE 22

Following the procedure described in Example 10 but starting from 1-naphthyl-acetamidoxime and using piperidine as amine component O-(3-piperidino-2-hydroxy-1-propyl)-1-naphthyl-acetamidoxime hydrochloride is prepared. Melting point: 177° to 179° C. (from abs. ethanol). Molecular weight: 377.89.

Elemental analysis for $C_{20}H_{28}N_3O_2Cl$: Calculated: C=63.57%; H=7.46%; N=11.12%; Cl=9.38%; Found: C=63.58%; H=7.59%; N=11.47%; Cl=9.60%.

EXAMPLE 23

To the mixture of 4.0 g. of benzamidoxime, 10 ml. of water and 4.5 g. of epichlorohydrine 20 ml. of 10% sodium hydroxide solution is added under stirring at room temperature dropwise, for one hour. The reaction mixture is then stirred for further two hours, 4.5 g. of piperidine are added dropwise and stirring is continued for eight subsequent hours. The oily substance is extracted with benzene. Upon evaporating the benzene solution 6.2 g. of O-(3-piperidino-2-hydroxy-1-propyl)-benzamidoxime are obtained. The compound is identical with the product of Example 1.

EXAMPLE 24

6.8 g. of benzamidoxime are dissolved in 40 ml. of 10% sodium hydroxide solution and 9.5 g. of epichlorohydrine are added under stirring. The reaction is exoterm, and therefore the temperature of the mixture is kept at 30° to 35° C. by external cooling. After stirring for two hours 8.6 g. of piperidine are added dropwise. The mixture is stirred for subsequent two hours and the oily substance obtained is extracted with benzene. Upon evaporating of benzene 8.2 g. of O-(3-piperidino-2-hydroxy-1-propyl)-benzamidoxime are obtained. The compound formed is identical with the product of Example 1.

EXAMPLE 25

6.8 g. of benzamidoxime are dissolved in 40 ml. of 10% sodium hydroxide solution and 9.5 g. of epichlorohydrine in 20 ml. of benzene are added under vigorous stirring dropwise. After stirring for four hours 8.6 g. of piperidine are added dropwise and the mixture is stirred at room temperature for subsequent eight hours. The benzene phase is separated, the aqueous layer is extracted with benzene. Upon evaporation the combined benzene solutions O-(3-piperidino-2-hydroxy-1-propyl)-benzamidoxime is obtained. This compound is identical with the product of Example 1.

EXAMPLE 26

6.8 g. of benzamidoxime are dissolved in the mixture of 20 ml. of 10% sodium hydroxide solvent and 20 ml. of ethanol, and 9.5 g. of epichlorohydrine are added under stirring, dropwise. After stirring for two hours at room temperature 8.6 g. of piperidine are added dropwise and the stirring is continued for eight subsequent hours. The methanol is evaporated in vacuo and the oily substance is extracted with benzene. Upon evaporating the benzene solution 7.2 g. of O-(3- piperidino-2-hydroxy-1-propyl)-benzamidoxime are obtained. This compound is identical with the product of Example 1.

EXAMPLE 27

To the solution of 5.2 g of 3,4-dimethoxyphenyl-acetamidoxime in 20 ml. of dimethyl sulfoxide 2.4 g. of sodium terc.buthylate are added under stirring. 3.0 g. of epichlorohydrine are then added dropwise, the mixture is stirred at room temperature for two hours. Thereafter, the solution of 2.5 g. of piperidine in 60 ml. of acetone is added and the reaction mixture is refluxed for eight hours, whereupon 120 ml. of ethyl acetate are added. Upon introducing hydrochloric acid gas 4.4 g. of O-(3-piperidino-2-hydroxy-1-propyl)-3,4-dimethoxyphenyl-acetamidoxime dihydrochloride are obtained in crystalline form. This salt is identical with the product of Example 2.

EXAMPLE 28

Following the procedure of the Example 6 but starting from 2-phenyl-propionamidoxime and 3-piperidino-2-hydroxy-1-chloro-propane O-(3-piperidino-2-hydroxy-1-propyl)-2-phenyl-propionamidoxime dihydrochloride are obtained. Melting point: 225° C. (from isopropanol).

Elemental analysis: Calculated: C=53.96%; H=7.73%; N=11.11%; Cl=18.74%; Found: C=54.27%; H=8.00%; N=10.86%; Cl=18.45%;

EXAMPLE 29

Following the procedure described in Example 6 but starting from 3-cyclohexylamino-2-hydroxy-1-chloro-propane (J. Org. Chem., 24, 615 (1959) and nicotinamidoxime O-(3-cyclohexylamino-2-hydroxy-1-propyl)-nicotinamidoxime is prepared. Melting point: 102° C.(from the mixture of benzene and toluene). Molecular weight: 292.37.

Elemental analysis for $C_{15}H_{24}N_4O_2$: Calculated: C=61.62%; H=8.27%; N=19.16%; Found: C=61.44%; H=8.23%; N=18.89%.

EXAMPLE 30

1.38 g. of racemic O-(3-piperidino-2-hydroxy-1-propyl)-benzamidoxime and 1.16 g. of d-camphorsulfonic acid are dissolved in 20 ml. of hot ethanol and the solution is evaporated in vacuo. The residue is recrystallized first from buthyl acetate and then from ethyl acetate. 0.4 g. of d-O-(3-piperidino-2-hydroxy-1-propyl)-benzamidoxime d-camphorsulfonate are obtained. Melting point: 132° C.

From the salt obtained the base is liberated by a conventional technique and the base obtained is transformed into a hydrochloric acid salt. The melting point of the hydrochloric acid salt is: 196° C. $|\alpha|_{559nm} = +6.3°$ (c=1%; water).

EXAMPLE 31

1.15 g. sodium metal are dissolved in 100 ml. of abs. ethanol and 12.0 g. of 3,3-diphenyl-propionamidoxime are added. While boiling, there are added 13.2 g. of 2-phenyl-3-isopropyl-5-chloromethyl-oxazolidine dropwise and the reaction mixture is boiled for subsequent 16 hours. The solvent is evaporated, 110 ml. of 5 n hydrochloric acid solution are added to the residue and it is refluxed for one hour. The solution is extracted with ethylene acetate, decolored with animal charcoal and adjusted to alkaline with 10% sodium hydroxide solution. The oil product is extracted with ethyl acetate, the extract is dried over dry sodium sulfate, and finally the solvent is evaporated. The residue is dissolved in acetone and the solution of hydrochloric acid in acetone is added. 7.0 g. of O-(3-isopropylamino-2-hydroxy-1-propyl)-3,3-diphenylpropion-amidoxime dihydrochloride are obtained. This compound is identical with the product of Example 14. Melting point: 179° C.

EXAMPLE 32

Following the procedure of Example 31 but starting from 2-phenyl-propionamidoxime and 2-phenyl-3-isopropyl-5-chloromethyl-oxazolidine O-(3-isopropylamino-2-hydroxy-1-propyl)-2-phenyl-propionamidoxime dihydrochloride hemihydrate is obtained. Melting point: 168° C. (from the mixture of acetone and isopropanol). Molecular weight: 361.31.

Elemental analysis for $C_{15}H_{27}N_3O_2Cl_2$, 0.5 $H_2O$: Calculated: C=49.86% H=7.81%; N=11.63%; Cl=19.63%; Found: C=49.79%; H=7.57%; N=11.61%; Cl=19.50%.

EXAMPLE 33

Following the procedure described in Example 31 but starting from benzamidoxime and 2-phenyl-3-isopropyl-5-chloromethyl-oxazolidine O-(3-isopropylamino-2-hydroxy-1-propyl)-benzamidoxime dihydrochloride hemihydrate is prepared. Melting point: 173° to 174° C. Molecular weight: 333.26.

Elemental analysis for $C_{13}H_{23}N_3O_2Cl_2 \cdot 0.5H_2O$: Calculated: C=46.85%; H=7.26%; N=12.61%; Cl=21.28%; Found: C=47.05%; H=7.13%; N=12.41%; Cl=21.54%.

What we claim is:

1. A compound of the formula $$R^4-(CH)_m-(CH)_n-\underset{\underset{OH}{|}}{\overset{R^5}{\underset{|}{}}}\overset{R^6}{\underset{|}{}}\overset{}{\underset{}{}}C-NH_2$$
$$\underset{}{\overset{}{}} \| $$
$$N-O-CH_2-CH-CH_2-N\underset{R^3}{\overset{R^2}{<}}$$

or a pharmaceutically acceptable salt thereof wherein
$R^2$ is hydrogen or alkyl having 1 to 5 carbon atoms;
$R^3$ is alkyl, having 1 to 5 carbon atoms, or phenyl each unsubstituted or substituted by hydroxyl or phenyl;
$R^4$ is unsubstituted or halogen-, $C_1$ to $C_4$ alkoxy or $C_1$ to $C_4$ alkyl mono- or disubstituted phenyl or napthyl;
$R^5$ is hydrogen or alkyl having 1 to 4 carbon atoms, or phenyl which can be mono- or disubstituted with halogen, alkoxy having 1 to 4 carbon atoms or alkyl having 1 to 4 carbon atoms;
$R^6$ is hydrogen, alkyl having 1 to 4 carbon atoms or phenyl;
m is 0, 1 or 2 and
n is 0, 1 or 2.

2. The compound defined in claim 1 wherein $R^2$ is hydrogen or alkyl having 1 to 5 carbon atoms and $R^3$ is alkyl having 1 to 5 carbon atoms unsubstituted or substituted by hydroxyl or a pharmaceutically acceptable salt thereof.

3. The compound defined in claim 1 wherein $R^2$ is hydrogen or alkyl having 1 to 5 carbon atoms; $R^3$ is alkyl having 1 to 5 carbon atoms unsubstituted or substituted by hyroxyl; and $$R^4-(CH)_m-(CH)_n-\underset{}{\overset{R^5}{\underset{|}{}}}\overset{R^6}{\underset{|}{}}$$

is selected from the group which consists of: phenyl, phenylmethyl, 1-naphthylmethyl, 1-phenylethyl, and 2,2-diphenylethyl; or a pharmaceutically acceptable salt thereof.

4. O-(3-diethylamino-2-hydroxy-1-propyl)-phenylacetamidoxime or a pharmaceutically acceptable salt thereof, as defined in claim 1.

5. O-(3-isopropylamino-2-hydroxy-1-propyl)-3,3-diphenylpropionamidoxime or a pharmaceutically acceptable salt thereof, as defined in claim 1.

6. O-(3-diethylamino-2-hydroxy-1-propyl)-3,3-diphenylpropionamidoxime or a pharmaceutically acceptable salt thereof, as defined in claim 1.

7. O-[3-N-methyl-N-(2-hydroxyethyl)-amino-2-hydroxy-1-propyl]-3,3-diphenyl-propionamidoxime or a pharmaceutically acceptable salt thereof, as defined in claim 1.

8. O-(3-isopropylamino-2-hydroxy-1-propyl)-2-phenylpropionamidoxime or a pharmaceutically acceptable salt thereof, as defined in claim 1.

9. O-(3-isopropylamino-2-hydroxy-1-propyl)-benzamidoxime or a pharmaceutically acceptable salt thereof, as defined in claim 1.

10. O-(3-diethylamino-2-hydroxy-1-propyl)-1-naphthylacetamidoxime or a pharmaceutically acceptable salt thereof, as defined in claim 1.

* * * * *